United States Patent [19]

Bartlett et al.

[11] Patent Number: 4,775,534

[45] Date of Patent: Oct. 4, 1988

[54] MITICIDAL COMPOSITION AND METHOD FOR CONTROLLING SPIDER MITE POPULATIONS

[75] Inventors: Ronald H. Bartlett, Glendale; Iain Weatherston, Phoenix; F. Gayle Kennedy, Glendale, all of Ariz.

[73] Assignee: Fermone Chemicals, Inc., Houston, Tex.

[21] Appl. No.: 826,844

[22] Filed: Feb. 5, 1986

[51] Int. Cl.$^4$ .............................................. A01N 25/18
[52] U.S. Cl. ................................ 424/410; 106/15.05; 424/DIG. 10; 424/419; 424/417; 424/420; 424/421; 514/965
[58] Field of Search ............... 514/965; 424/DIG. 10, 424/22, 23, 410, 419, 420, 421, 417; 106/15.05

[56] References Cited

U.S. PATENT DOCUMENTS

| | | | |
|---|---|---|---|
| 3,072,526 | 1/1963 | Butenandt et al. | 167/48 |
| 3,207,661 | 9/1965 | Curtis et al. | 167/33 |
| 3,323,898 | 6/1967 | Pierce | 71/64 |
| 3,576,834 | 4/1971 | Buchanan | 360/453 |
| 4,017,030 | 4/1977 | Coplan et al. | 239/44 |
| 4,122,165 | 10/1978 | Kinzer et al. | 424/84 |
| 4,536,206 | 8/1985 | Kubo et al. | 424/419 |
| 4,552,752 | 11/1985 | Amick | 424/419 |
| 4,554,155 | 11/1985 | Allan et al. | 424/419 |

FOREIGN PATENT DOCUMENTS

| | | |
|---|---|---|
| 477526 | 10/1976 | Australia . |
| 55847 | 9/1952 | France . |
| 2933757A1 | 3/1981 | Fed. Rep. of Germany . |
| 3207473A1 | 9/1982 | Fed. Rep. of Germany . |
| 48-26222 | 7/1973 | Japan . |
| 2018593 | 10/1979 | United Kingdom . |
| 2067406 | 7/1981 | United Kingdom . |
| 2095998B | 9/1984 | United Kingdom . |
| 2141932 | 1/1985 | United Kingdom . |

OTHER PUBLICATIONS

Regev & Cone, "Analysis of Pharate Female Twospotted Spider Mites For Nerolidol and Geraniol: Evaluation for Sex Attraction of Males," Environmental Entomology, Feb. 1976, vol. 5, No. 1, pp. 133–138.

Regev & Cone, "Evidence of Farnesol as a Male Sex Attractant of the Twospotted Spider Mite, Tetranychus urticae Koch (Acarina; Tetranychidae)", Environmental Entomology, Apr. 1975, vol. 4, No. 2, pp. 307–311.

Sonenshine et al., "Studies to Evaluate the Effectiveness of Sex Pheromone-Impregnated Formulations for Control of Populations of the American Dog Tick, Dermacentor variabilis (Say), (acari: Ixodidae), Experimental and Applied Acarology, 1 (1985), Elsevier Science Publishers B.V., Amsterdam. pp. 23–34.

Chemical Abstracts, vol. 84, No. 19, dated 5/10/76, Referencing Article by Regev and Cone Published in Environmental Entomology in 1976 Entitled "Analyses of Pharate Female Twospotted Spider Mites for Nerolidol and Geraniol: Evaluation for Sex Attraction of Males".

Primary Examiner—Ronald W. Griffin
Attorney, Agent, or Firm—Cahill, Sutton & Thomas

[57] ABSTRACT

A miticidal composition for controlling spider mite populations is formed by impregnating a controlled release substrate with farnesol and nerolidol to form a flowable liquid concentrate or wettable powder. The flowable liquid concentrate or wettable powder is added to a liquid spray base to which a miticide has been added, and mixed therewith to form the miticidal composition. The resulting composition is applied by conventional tank spray equipment to the foliage of plants or trees to control spider mite populations therein.

32 Claims, No Drawings

MITICIDAL COMPOSITION AND METHOD FOR CONTROLLING SPIDER MITE POPULATIONS

BACKGROUND OF THE INVENTION

1. Field of the Invention

The present invention relates generally to behavior modifying chemicals which influence the behavior of spider mites as well as to miticides used to kill spider mites, and more particularly, to a novel miticidal composition combining farnesol and/or nerolidol in a controlled release form with a miticide to enhance the effectiveness of the miticide in controlling spider mite populations.

2. Description of the Prior Art

Spider mites, belonging to that family of Acari known scientifically as Tetranychidae, are a common form of agricultural pest which damage the foliage of agricultural crops, trees and ornamentals. Two species of spider mites which are common are the carmine spider mite (*Tetranychus cinnabarinus*) and the two-spotted spider mite (*Tetranychus urticae*), both of which can inflict damage and reduce yields in cotton fields and other crops.

Various miticides are presently available to combat infestations of spider mites by killing such pests. One popular miticide is dicofol, commercially available from Rohm & Haas Company of Philadelphia, Pa. under the trademark "KELTHANE". Another popular miticide is a micronized form of sulfur, commercially available from Cumberland International of Houston, Tex. under the trademark "SULFLOX". A third type of popular miticide is 2-[4[1,1 dimethyl ethyl]phenoxy] cyclohexyl-2-propynyl sulfite, commercially available from Uniroyal Chemical, a division of Uniroyal, Inc. of Naugatuck Connecticut under the trademark "COMIIE". While such miticides are generally effective against spider mites in the short term, spider mites reproduce rapidly, and resistant strains develop an increased tolerance of such miticides over a period of approximately three years. It is believed that spider mites must actually come in physical contact with such miticides in order to be killed thereby. However as compared with other types of agricultural pests, spider mites move relatively little and are therefore less likely to come in physical contact with applied miticides unless relatively large amounts of such miticides are applied. Apart from the significant expense of applying large amounts of such miticides to the foliage of the plants or trees to be protected, it is believed that the application of large doses of such miticides results in the development of tolerance to such miticides more quickly.

It is known that certain chemicals are naturally produced by the female of certain insect species and other pests in order to attract the male. Such naturally occurring sex attractants are known as pheromones. Various types of such sex pheromones have been chemically extracted from the female of such insects. In some instances, such sex pheromones can be synthetically produced. In still other instances, chemicals which are not naturally present in a species of insect or other pest are nonetheless found to attract, repel, or otherwise influence the behavior of the male and/or female insect or other pest. Such naturally occurring or synthetically produced chemicals will sometimes be collectively referred to herein as behavior modifying chemicals.

It is known that certain behavior modifying chemicals, some naturally produced by spider mites, affect the behavior of spider mites, either by attracting, repelling or arresting the male of the species. Studies reported by Regev and Cone indicate that female two-spotted spider mites produce a sex pheromone which attracts the male of the species to a quiescent female deutonymph and serves to retain the attracted male until the emergence of the adult female, at which time mating normally occurs; extracts of the spider mite female deutonymphs showed the presence of the sesquiterpene alcohol farnesol. The study by Regev and Cone, entitled "Evidence of Farnesol As a Male Sex Attractant of the Two-Spotted Spider Mite, *Tetranychus urticae* Koch (Acarina: Tetranychidae)", Environmental Entomology, April 1985, Vol. 4, No. 2, pp. 307-311, indicated that certain isomers of synthetically produced farnesol, at particular concentrations, were effective in attracting male spider mites. A further study by Regev and Cone, "Analysis of Pharate Female Twospotted Spider Mites for Nerolidol and Geraniol: Evaluation for Sex Attraction of Males", Environmental Entomology, February 1976, Vol. 5, No. 1, pp. 133-138, also revealed that the two-spotted spider mite female deutonymph also contains the sesquiterpene alcohol nerolidol; their study indicated that synthetic nerolidol, at particular concentrations, served to attract male two-spotted spider mites.

Both of the above-referenced studies reported by Regev and Cone reference other studies wherein it is reported that farnesol and/or nerolidol act as attractants for higher insects such as bees and moths. However, Regev and Cone state that, in the case of higher insects, the sex attractant is airborne and detected by the male at a distance. In contrast, Regev and Cone report that an airborne sex attractant would not be of great advantage in the case of the spider mite because most offspring live in the same site where eggs are laid. Regev and Cone explain that, if the mother is fertilized, both sexes are produced from those eggs, hence, mates are not far from each other to necessitate an airborne kind of sex attractant. Regev and Cone further state that, with respect to the two-spotted spider mite, it is the tactile chemical stimulus which is important insofar as attracting male spider mites.

The concept of combining volatile sex attractants with insecticides for controlling populations of higher insects is known. For example, U.S. Pat. No. 4,122,165, issued to Kinzer et al., and Australian Patent No. 477,526, issued to Thuron Industries, Inc., both describe the combination of the sex pheromone cis-9-tricosene (muscalure) with an insecticide to control house fly (*Musca domestica*) populations.

Higher insects such as bees, moths and house flies, are highly mobile, and the male and female of the species must mate in order to reproduce. Given such characteristics, it is not surprising that airborne sex attractants have proven effective to enhance the effect of pesticides on such insect species. In contrast, spider mites, which are not true insects, exhibit parthenogenesis, i.e., female spider mites can reproduce males without first mating with a male spider mite. In addition, mites are relatively small and do not move far from the site from which they are hatched. Furthermore, as set forth above with respect to the studies conducted by Regev and Cone, sex attractants in spider mites operate principally by tactile chemical stimulus, leading Regev and Cone to conclude that an airborne sex attractant would not be of great advantage in the case of the spider mite.

In view of the distinct differences in the mating patterns, operation of sex attractants, and general behavior as between spider mites and higher insect forms, the ability of spider mite behavior modifying chemicals to influence the effectiveness of miticides is not readily apparent and could not have been predicted.

It is an object of the present invention to provide a miticidal composition which includes a miticide and which provides significantly improved effectiveness to control spider mite populations as compared with usage of the miticide alone.

It is another object of the present invention to provide such a miticidal composition which allows lesser application rates of conventional miticides than those presently used without reducing the level of control of spider mite populations.

It is still another object of the present invention to provide such a miticidal composition including a behavior modifying chemical which tends to increase the likelihood that spider mites will come in contact with an applied miticide.

It is a further object of the present invention to provide such a miticidal composition in a form which slowly releases such a behavior modifying chemical to prevent the same from dissipating too rapidly.

It is still a further object of the present invention to provide compositions in the form of solutions, emulsions, dispersions, powders, dusts, granules, pellets and the like adapted to be combined with a conventional miticide in order to easily form such an improved miticidal composition.

Yet another object of the present invention is to provide a method of controlling spider mite populations in the foliage of agricultural fields, trees, greenhouses, gardens and homes wherever there are plants susceptible to spider mite damage, through the application of such a miticidal composition.

These and other objects of the present invention will become more apparent to those skilled in the art as the description thereof proceeds.

SUMMARY OF THE INVENTION

Briefly described, and in accordance with one embodiment thereof, the present invention relates to a miticidal composition adapted to be sprayed onto foliage to control spider mite populations, the miticidal composition including a liquid spray base and a miticide mixed therewith, together with a controlled release substrate impregnated with, or otherwise combined with, a behavior modifying chemical including farnesol and/or nerolidol. The controlled release substrate serves as a carrier to slowly release the behavior modifying chemical after the miticidal composition has been applied to the foliage, thereby increasing movement of spider mites and increasing the likelihood of physical contact between such spider mites and the miticide incorporated within the miticidal composition. Conventional miticides such as those sold under the trademarks "KELTHANE", "SULFLOX", and "COMITE", may be incorporated within such a miticidal composition. The aforementioned controlled release substrate preferably contains at least 100 milligrams of farnesol and at least 50 milligrams of nerolidol for each one-acre application of the miticidal composition.

The aforementioned controlled release substrate may be in either solid or liquid form to provide compositions in the form of solutions, emulsions, dispersions, flowable liquid concentrates, wettable powders, dusts, granules, pellets and the like. Preferred forms of the controlled release substrate are flowable liquid concentrates and wettable powders. Solid controlled release substrates include porous particulates such as silica, perlite, talc, clay, pyrophyllite, diatomaceous earth, gelatin and gels, polymers, polyurea, nylon, polymeric particles, cellulose, finely ground corn cobs and the like. Liquid forms of such a controlled release substrate include vegetable and/or mineral oils, preferably containing surface active agents to render the composition readily dispersable in water; such agents include wetting agents, emulsifying agents, dispersing agents and the like. Microcapsules may also serve as suitable controlled release substrates. After being combined with the appropriate behavior modifying chemical, such controlled release substrates may be packaged, for example as flowable liquid concentrates or wettable powders, and shipped to the site where the miticidal composition is to be mixed and applied, or alternatively, the impregnated controlled release substrate can be mixed at the production plant with a suitable miticide and packaged for shipment as a combined product.

Another aspect of the present invention relates to the composition of, and method of formulating, such a flowable liquid concentrate containing a controlled release substrate impregnated with behavior modifying chemicals for combatting spider mites. The flowable liquid concentrate is formed by first impregnating farnesol, nerolidol, and/or other behavior modifying chemical influential on spider mites, within the controlled release substrate, such as by spraying the behavior modifying chemical under pressure onto the surface of a porous particulate substrate as the same is blended. The impregnated porous particulate substrate is intermixed with a stirred water based emulsion. After the impregnated porous particulate substrate has been sufficiently intermixed with the water based emulsion, a gelling agent is added to thicken the water based emulsion to form a flowable liquid concentrate containing the behavior modifying chemical. The flowable liquid concentrate may then be readily shipped for subsequent mixing with a miticide and spray base at the site where the miticidal composition is to be applied.

DETAILED DESCRIPTION OF THE PREFERRED EMBODIMENTS

As mentioned above, the miticidal composition described herein is preferably formed by intermixing a controlled release substrate containing the behavior modifying chemical in a controlled release form with a liquid spray base with which a miticide has been mixed. A preferred method of making a flowable liquid concentrate containing such a controlled release substrate will now be described.

First, a quantity of a controlled release substrate is obtained to serve as a controlled release carrier for the behavior modifying chemical. The controlled release substrate may be in the form of a particulate substrate that is finely ground and may consist of fine particles of silica (such as that commercially available from PPG Industries, Inc. of Pittsburgh, Pa. under the trademark "HYSIL"), perlite, talc, clay, pyrophyllite, diatomaceous earth, gelatin, polyurea, cellulose, finely ground corn cobs, microcapsules, and the like. While the present description is directed to the use of a solid particulate as a controlled release substrate, liquid controlled release substrates, such as vegetable and/or mineral oils may also be used. In this event, one or more surface active agents (such as wetting agents, emulsifying agents, dispersing agents, and the like) are added to render the composition readily dispersable in water.

The selected particulate substrate is disposed in a ribbon blender, such as a Type 3 ribbon blender available from Sproule Waldron & Company of Muncie, Pa. While the ribbon blender is operating and blending the particulate substrate, a quantity of the behavior modifying chemical influential on spider mites, such as farnesol and/or nerolidol, is atomized and sprayed under pressure onto the surface of the blended particulate substrate for coating the same and allowing the behavior modifying chemical to become impregnated within the porous particulate substrate. The microscopic pores of the particulate substrate absorb and store the behavior modifying chemical for controllably releasing the same after the miticidal composition described herein is applied in the field.

In the preferred embodiment of the present invention, both farnesol and nerolidol are used as behavior modifying chemicals and are impregnated within the selected particulate substrate or other controlled release substrate. Both farnesol and nerolidol are commercially available in liquid form from Givaudan Corp. of Clifton, N.J.

Following the operation of spraying the behavior modifying chemical onto the blended particulate substrate, a water based emulsion, such as may be obtained from SDS Biotec of Cleveland, Ohio; Witco Chemical Corp. of New York, N.Y.; or Desoto, Inc. of Des Plaines, Ill. is stirred for approximately ten minutes at room temperature. In the preferred embodiment of the present invention, approximately 250 gallons of the water based emulsion is prepared, and approximately 84 pounds of the impregnated particulate substrate is added thereto; the mixture is stirred for an additional ten minutes at room temperature, at which time a gelling agent is added and stirring continued for a further period of twenty minutes to yield approximately 250 gallons of the flowable liquid concentrate containing the behavior modifying chemical. Suitable gelling agents include commercially available cellulose derivatives, bentonite and attapulgite clays, and xanthan gums.

Optionally, conventional pest control adjuvants, diluents, modifiers, or conditioning agents may be added to the aforementioned flowable liquid concentrate. Examples of such adjuvants include antifoaming agents (such as dimethylpolysiloxane), pH buffering agents (such as alkyarylpolyethoxyethanal) and compatibility agents (such as alcohol sulfates). Such adjuvants are commercially available from Kalo AG Chem, Inc. of Overland Park, Kans. An example of a desirable diluent is a spreader sticker agent, such as alkylarylpolyoxyethylene glucose available from Rigo Company of Buckner, Ky.

The resulting flowable liquid concentrate formulated in the above-described manner may be sold and shipped in relatively small quanitites, such as one gallon containers, for mixing at the site where mite populations are to be controlled. The flowable liquid concentrate may be mixed at the site with a liquid spray base and a conventional miticide in a manner which will be described in greater detail below.

When formulating the flowable liquid concentrate described above, a sufficient quantity of the porous particulate substrate impregnated with both farnesol and nerolidol, is added to the water based emulsion to cause each two ounce portion of the flowable liquid concentrate to contain at least 100 milligrams of farnesol and 50 milligrams of nerolidol. As is discussed below, it is recommended that two to six liquid ounces of the flowable liquid concentrate be used for each acre of foliage to be treated, when mixing the miticidal composition. Each two ounce portion of the flowable liquid concentrate preferably includes at least 100 milligrams of farnesol and 50 milligrams of nerolidol so that each acre treated receives at least a corresponding amount of such behavior modifying chemicals.

While the description above relates to the formulation of a controlled release substrate impregnated with the behavior modifying chemical in the form of a flowable liquid concentrate, the controlled release substrate, after being combined with the behavior modifying chemicals, can also be provided in the form of solutions, emulsions, dispersions, powders, dusts, granules, pellets and the like. Those skilled in the art are generally familiar with methods of formulating compositions in such forms for agricultural use. General teachings as to methods of preparation of such compositions in the form of solutions, emulsions, dispersions, powders, dusts, granules, pellets and the like may be found in *Chemicals For Crop Protection And Pest Control* by Green, Hartley and West, Pergamon Press, Oxford 1977, the disclosure of which is hereby incorporated by reference. More detailed information concerning the formulation of dusts, wettable powders and granules may be found in the technical article entitled "Formulation of Pesticidal Dusts, Wettable Powders and Granules", authored by J. A. Polon, appearing in *Pesticide Formulations,* edited by W. Van Valkenberg, published by Marcel Dekker, New York, N.Y. 1973, pp. 143–234, the disclosure of which is hereby incorporated by reference. Further information concerning the preparation of flowable pesticide formulations may be found in "Flowable Pesticide Formulations: Development, Process and the Need for Standard Testing Procedures", authored by C. G. Halliday, appearing in *Pesticide Formulations and Application Systems,* edited by K. G. Seymour, published by American Society of Testing Materials, STP 795, 1983, pp. 45–52, the disclosure of which is hereby incorporated by reference. Additional information concerning the use of microcapsules as controlled release carriers may be found in "Microencapsulized Pesticides", authored and edited by H. B. Scher, appearing in *Controlled Release Pesticides,* published by American Chemical Society, Washington, D.C. 1977, pp. 126–144, the disclosure of which is hereby incorporated by reference.

The various compositions of the controlled release substrate and combined behavior modifying chemical, whether in the form of solutions, emulsions, dispersions, flowable liquid concentrates, wettable powders, dusts, granules, or pellets, may all include conventional pest control adjuvents, diluents, modifiers or conditioning agents, and either packaged for shipment to the site of application or combined at the production plant with a suitable miticide and liquid spray base for shipment in ready-to-use form.

In those instances wherein the improved miticidal composition described herein is mixed at the application site, the user first selects a suitable liquid spray base, such as water or emulsifiable vegetable oil, and adds the same to a mixing tank. A conventional miticide, such as those sold under the trademarks "KELTHANE", "SULFLOX" or "COMITE" is then added to the mixing tank and mixed with the liquid spray base in the proportions generally recommended by the manufacturers of such miticides. The controlled release substrate described above and containing the behavior modifying chemical is added last to the mixing tank and mixed thoroughly within the liquid spray base. The resulting miticidal composition may then be applied to spider mite infested foliage by any conventional hand operated, ground-based or aerial spray application equipment. Best results are obtained if the miticidal composition is applied to the foliage immediately after mixing When the controlled release substrate is provided as flowable liquid concentrate, 2 to 6 ounces of the concentrate are required per acre to be treated with the miticidal composition Manufacturers of common miticides generally recommend that approximately 3 gallons of mixed miticide spray be applied for every acre to be treated; accordingly, 2 to 6 liquid ounces of flowable liquid concentrate containing the behavior modifying chemical will be added to the spray tank for each 3 gallons of miticidal composition spray. Greater amounts of flowable liquid concentrate may be required as spider mite population pressure increases, or when applying parts per million. As described above, preferred formulations of the miticidal composition include at least 100 milligrams of farnesol and 50 milligrams of nerolidol.

Field Test Data

A first field test was conducted to determine the effectiveness of the flowable liquid concentrate described above, when used in conjunction with three popular miticides, in controlling carmine spider mite populations in a cotton field. Four 0.1 acre plots within the cotton field were selected to conduct the field test. Each of the various miticidal compositions was applied as a ground spray at the equivalent rate of 10 gallons per acre. Each miticidal composition was applied on a starting date (day one), reapplied nine days later (day nine) and reapplied once more six days following (day fifteen). The evaluation of each miticidal composition was made by the leaf sampling technique and by taking the average number of spider mites counted on each sampled leaf. Within the test data table below are reported the test results obtained for various application rates of different miticides with and without the addition of the behavior modifying chemical, as well as the leaf counts for an untreated plot of the cotton field.

| FIELD TEST NO. 1 - DATA TABLE | | | | | |
|---|---|---|---|---|---|
| | | Average no. spider mites/leaf | | | Mean |
| TREATMENT | RATE/ACRE | DAY 9 | DAY 15 | DAY 23 | Average |
| Kelthane only | 2.0 pt. | 20 | 2 | 2 | 8.0 |
| Kelthane only | 1.0 pt. | 24 | 11 | 10 | 15.0 |
| Kelthane + | 1.0 pt. | | | | |
| BMC | 2 oz | 2 | 2 | 4 | 2.67 |
| Sulflox only | 1.0 pt. | 6 | 15 | 10 | 10.33 |
| Sulflox + | 1.0 pt. | | | | |
| BMC | 2 oz | 2 | 3 | 7 | 4.0 |
| Comite only | 1.0 pt. | 12 | 4 | 8 | 8.0 |
| Comite + | 1.0 pt. | | | | |
| BMC | 2 oz | 0 | 0 | 2 | 0.67 |
| Untreated check | | 31 | 28 | 30 | 29.67 | spray volumes in excess of 3 gallons per acre, as might be required when spraying trees. A minimum of two applications of the above-described miticidal composition are recommended at intervals corresponding to those recommended by the selected miticide manufacturer. Further applications of the miticidal composition may be used when needed or following rain storms.

The relative benefits of including the behavior modifying chemical, such as farnesol and/or nerolidol, within the miticidal composition depend in part upon the ultimate concentrations of such behavior modifying chemicals within the final mixed spray that is applied to the foliage where spider mite populations are present. When farnesol is incorporated within the flowable liquid concentrate as an active behavior modifying chemical for spider mites, the ultimate concentration of farnesol within the final spray mix should be at least 15 parts per million. In addition, concentrations of farnesol in the final spray mix exceeding 200 parts per million do not appear to improve the effectiveness of the miticidal composition. In those instances where nerolidol is incorporated within the flowable liquid concentrate as an active behavior modifying chemical, concentrations of 10 parts per million of nerolidol relative to the final spray mix appear to be desirable, while concentrations of nerolidol in the final spray mix at or exceeding 100 parts per million do not appear to provide any beneficial effect. The preferred range of nerolidol content, relative to the final spray mix is 5 parts per million to 50

As shown in the above table, leaf samples are reported as counted on day nine (immediately before reapplication), day fifteen (immediately before reapplication) and on day twenty-three (eight days after the last application. Normal rates of application of Kelthane, Sulflox and Comite miticides, as recommended by their respective manufacturers, are 2-3 pints per acre, 2-4 pints per acre, and 1-3 pints per acre, respectively depending upon the crops being treated.

As noted in the above table, the use of Kelthane brand miticide alone at the rate recommended by its manufacturer successfully controlled spider mite populations. However, when the rate of application of Kelthane brand miticide alone was reduced to one-half of the lowest rate recommended by its manufacturer, it did not provide acceptable control. On the other hand, the use of Kelthane brand miticide at one-half the manufactuer's lowest suggested application rate, when combined with 2 ounces per acre of the behavior modifying chemical concentrate described above exhibited superior control over spider mite populations as compared with the mean average obtained through the use of the Kelthane brand miticide alone at the manufacturer's recommended rate. As further roted in the table, the addition of 2 ounces per acre of the behavior modifying chemical concentrate described above to Sulflox brand miticide and Comite brand miticide also brought about greatly enhanced spider mite population control. The above test results appear to indicate that the amount of miticide normally recommended by the manufacturer may be reduced when combined with the above-described behavior modifying chemical concentrate, achieving superior levels of spider mite control.

A second field test was conducted to determine the effectiveness of the miticidal composition described herein upon the two-spotted spider mite within cotton fields. The test was conducted on 25 foot, single rows of cotton plants, such tests being replicated on three such rows of the cotton field. The various miticidal compositions used in the test were applied by a backpack sprayer at the equivalent rate of 50 gallons of spray per acre. The effectiveness of each miticidal composition was evaluated by microscopically examining twelve leaves from each of the replicate test rows. Test results are reported in the table below for Kelthane brand miticide only, Comite brand miticide only, Kelthane brand miticide in conjunction with the behavior modifying chemical concentrate, as well as an untreated check. Spider mite leaf counts were made immediately prior to application of the spray mix, as well as seven days later, in order to determine the effectiveness of each miticidal composition.

| | | AV. NO. MITES/LEAF | | |
|---|---|---|---|---|
| TREATMENT | RATE/ ACRE | Pre-spray | 7 days post spray | % REDUC- TION |
| Kelthane only | 1.5 pts. | 9.2 | 5.7 | 38 |
| Kelthane only | 3.0 pts. | 11.9 | 2.3 | 81 |
| Kelthane + BMC | 1.0 pt. 4 oz | 12.6 | 2.0 | 84 |
| Kelthane + BMC | 1.125 pts. 4 oz | 9.2 | 5.7 | 38 |
| Comite only | 3.0 pts. | 13.5 | 5.7 | 58 |
| Untreated check | | 7.6 | 15.7 | (206) |

FIELD TEST NO. 2 - DATA TABLE

As shown in the above table, the use of Kelthane brand miticide at the rate of approximately one pint per acre, when combined with four ounces of the behavior modifying chemical concentrate per acre, provides equal or greater control over two-spotted spider mite populations than Kelthane brand miticide applied alone at the rate of one and a half and three pints per acre.

The above table also reflects that the use of Kelthane brand miticide at the rate of one pint per acre, when combined with four ounces per acre of behavior modifying chemical concentrate, at least in one case, provided greater control than the manufacturer's highest recommended application rate of Comite brand miticide when used alone.

It is theorized that the incorporation of behavior modifying chemicals such as farnesol and/or nerolidol, within the miticidal composition increases the natural, instinctive movement behavior and search activities of the male spider mite. Resulting increased random movement brings the male spider mite into more frequent and prolonged contact with the miticide applied to the foliage. The resulting increased exposure to the miticide enhances the effect thereof, thereby reducing infestation and crop damage.

Use of the miticidal composition described herein is believed to enhance the level of spider mite control provided by common miticides when treating such crops as alfalfa, clover, cotton, peanuts, sorghum, citrus, beans, blackberries, raspberries, corn, cucumbers, melons, pumpkins, squash, eggplant, peppers tomotoes, hops, strawberries, ornamentals, grapes, as well as fruit tree and nut tree crops.

While the present invention has been described with reference to the preferred embodiments thereof, the description is for illustrative purposes only and is not to be construed as limiting the scope of the invention. Various modifications and changes may be made by those skilled in the art without departing from the true spirit and scope of the invention as defined by the appended claims.

We claim:

1. A composition adapted to be combined with a miticide and applied to the foliage of plants and trees for increasing the effectiveness of the miticide against spider mites, said composition comprising in combination:
   (a) a controlled release substrate;
   (b) a behavior modifying chemical chosen from the group consisting of farnesol and nerolidol, said behavior modifying chemical being intermixed with said controlled release substrate for being slowly and continuously released therefrom.

2. The composition recited by claim 1 further including:
   (a) a water based emulsion with which said controlled release substrate is intermixed; and
   (b) a gelling agent intermixed with said water based emulsion for thickening said water based emulsion to form a flowable liquid concentrate.

3. The composition recited by claim 2 wherein said controlled release substrate is a porous particulate substrate chosen from a group of porous particulate substrates consisting of silica, perlite, talcs, clays, pyrophyllite, diatomaceous earth, gelatin, polymeric particles, and ground corn cobs.

4. The composition recited by claim 2 wherein said controlled release substrate is chosen from the group consisting of porous particulates, oils, gels, polymers, and microcapsules.

5. The composition as recited by claim 2 wherein each 2 fluid ounce portion of said composition includes at least 100 milligrams of farnesol and 50 milligrams of nerolidol.

6. The composition recited by claim 1 wherein said controlled release substrate is a porous particulate substrate impregnated with said behavior modifying chemical to form a wettable powder.

7. The composition recited by claim 6 wherein said porous particulate substrate is chosen from a group of porous particulate substrates consisting of silica, perlite, talcs, clays, pyrophyllite, diatomaceous earch, gelatin, polymeric particles, and ground corn cobs.

8. The composition recited by claim 6 wherein said behavior modifying chemical includes farnesol and nerolidol.

9. A miticidal composition adapted to be applied to the foliage of plants and trees to control spider mite populations, said miticidal composition comprising in combination:
   (a) a controlled release substrate;
   (b) a behavior modifying chemical chosen from the group consisting of farnesol and nerolidol, said behavior modifying chemical being intermixed with said controlled release substrate; and
   (c) a miticide.

10. The miticidal composition recited by claim 9 including a liquid spray base in which said controlled release substrate and said miticide are intermixed to provide said miticidal composition in a sprayable form.

11. The miticidal composition recited by claim 10 wherein said liquid spray base is a member of a group consisting of water and emulsifiable vegetable and/or mineral oils.

12. The miticidal composition recited by claim 10 wherein said said miticidal composition includes at least 100 milligrams of farnesol and 50 milligrams of nerolidol for each 3 gallons of said miticidal composition.

13. The miticidal composition recited by claim 9 wherein said controlled release substrate is a porous particulate substrate which slowly and continuously releases said behavior modifying chemical therefrom.

14. The miticidal composition recited by claim 13 wherein said porous particulate substrate is chosen from a group of porous particulate substrates consisting of silica, perlite, talcs, clays, pyrophyllite diatomaceous earth, gelatin, polymeric particles, and ground corn cobs.

15. The miticidal composition recited by claim 9 wherein said controlled release substrate is chosen from the group consisting of porous particulates, oils, gels, polymers, and microcapsules.

16. A method of controlling spider mite populations in the foliage of plants and trees by improving the effectiveness of miticides, comprising the steps of:
 (a) providing a liquid spray base;
 (b) intermixing with the liquid spray base a miticide;
 (c) further intermixing with the liquid spray base a composition containing a controlled release substrate and a behavior modifying chemical chosen from the group consisting of farnesol and nerolidol, said behavior modifying chemical being intermixed with said controlled release substrate, said further intermixing step forming a miticidal composition;
 (d) spraying the miticidal composition formed by said further intermixing step upon the foliage of the 17. The method recited by claim 16 wherein said further intermixing step includes the step of intermixing with the liquid spray base a sufficient quantity of said composition containing said behavior modifying chemical to provide at least 100 milligrams of farnesol and 50 milligrams of nerolidol for each 3 gallons of said miticidal composition.

18. The method recited by claim 16 wherein said step of intermixing a miticide with the liquid spray base includes the step of intermixing with the spray base a miticide that is a member of a group of miticides consisting of dicofol, micronized sulphur and 2-[4-[1,1 dimethy ethyl]phenoxy]cyclohexyl-2-prophynyl sulfite.

19. The composition as recited by claim 1 wherein said behavior modifying chemical includes farnesol and nerolidol.

20. A method of controlling spider mite populations in the foliage of plants and trees which comprises spraying upon the foliage of the plants or trees where it is desired to control spider mite populations sufficient amounts of a miticidal composition comprising in combination:
 a. a controlled release substance;
 b. farnesol and nerolidol as behavior modifying chemical intermixed with said controlled release substance for being slowly and continuously released therefrom; at least 100 milligrams of farnesol and 50 milligrams of nerolidol being applied for each 1-acre application of said composition.

21. The method recited by claim 20 wherein said miticidal composition further includes a miticide.

22. The method recited by claim 21 wherein said miticide is a member of a group of miticides consisting of dicofol, micronized sulphur and 2-[4-[1,1 dimethyl ethyl] phenoxy] cyclohexyl-2-prophynyl sulfite.

23. A method of controlling spider mite populations in the foliage of plants and trees by improving the effectiveness of miticides, comprising the steps of:
 a. providing a liquid spray base;
 b. intermixing with the liquid spray base a a miticide;
 c. further intermixing with the liquid spray base a composition containing a controlled release substrate and behavior modifying chemicals including farnesol and nerolidol, said behavior modifying chemicals being intermixed with said controlled release substrate, said further intermixing step forming a miticidal composition; and
 d. spraying the miticidal composition formed by steps a, b, and c above upon the foliage of the plants or trees where it is desired to control spider mite populations.

24. The method as recited by claim 23 wherein said spraying step includes the step of spraying upon the foliage sufficient amounts of the miticidal composition to apply at least 100 milligrams of farnesol and 50 milligrams of nerolidol for each 1-acre application of said miticidal composition.

25. The method recited by claim 23 wherein said step of intermixing a miticide with the liquid spray base includes the step of intermixing with the spray base a miticide that is a member of a group of miticides consisting of dicofol, micronized sulphur and 2-[4-[1,1 dimethy ethyl] phenoxy] cyclohexyl-2-prophynyl sulfite.

26. A miticidal composition adapted to be applied to the foliage of plants and trees to control spider mite populations, said miticidal composition comprising in combination:
 a. a controlled release substrate;
 b. behavior modifying chemicals including farnesol and nerolidol, said behavior modifying chemicals being intermixed with said controlled release substrate; and
 c. a miticide.

27. The miticidal composition recited by claim 26 including a liquid spray base in which said controlled release substrate and said miticide are intermixed to provide said miticidal composition in a sprayable form.

28. The miticidal composition recited by claim 27 wherein said liquid spray base is a member of a group consisting of water and emulsifiable vegetable and/or mineral oils.

29. The miticidal composition recited by claim 26 wherein said controlled release substrate is a porous particulate substrate which slowly and continuously releases said bahavior modifying chemicals therefrom.

30. The miticidal composition recited by claim 29 wherein said porous particulate substrate is chosen from a group of porous particulate substrates consisting of silica, perlite, talcs, clays, pyrophyllite, diatomaceous earth, gelatin, polymeric, particles, and ground corn cobs.

31. The miticidal composition recited by claim 26 wherein said controlled release substrate is chosen from the group consisting of porous particulates, oils, gels, polymers, and microcapsules.

32. The miticidal composition recited by claim 26 wherein said miticide is a member of a group of miticides consisting of dicofol, micronized sulphur and 2-[4-]1,1 dimethyl ethyl ] phenoxy] cyclohexyl-2-prophynyl sulfite.

* * * * *

UNITED STATES PATENT AND TRADEMARK OFFICE
CERTIFICATE OF CORRECTION

PATENT NO. : 4,775,534

DATED : October 4, 1988

INVENTOR(S) : Ronald H. Bartlett, Iain Weatherston, F. Gayle Kennedy

It is certified that error appears in the above-identified patent and that said Letters Patent is hereby corrected as shown below:

Col 11, Line 51, "prophynyl" should read --propynyl--;

Col 12, Line 4, "prophynyl" should read --propynyl--;

Col 12, Line 32, "prophynyl" should read --propynyl--;

Col 12, lines 66-67, "prophynyl" should read --propynyl--.

Signed and Sealed this

Eleventh Day of July, 1989

Attest:

DONALD J. QUIGG

Attesting Officer

Commissioner of Patents and Trademarks